United States Patent [19]

Okutsu

[11] Patent Number: 4,819,620
[45] Date of Patent: Apr. 11, 1989

[54] ENDOSCOPE GUIDE PIPE

[76] Inventor: Ichiro Okutsu, 1-13-15, Kita-Ohtsuka, Toshima-ku, Tokyo, Japan

[21] Appl. No.: 85,060

[22] Filed: Aug. 13, 1987

[30] Foreign Application Priority Data

Aug. 16, 1986 [JP] Japan .............................. 61-191201

[51] Int. Cl.$^4$ ................................................ A61B 1/00
[52] U.S. Cl. ............................................ 128/4; 128/6
[58] Field of Search ..................... 128/3, 4, 5, 6, 7, 8; 356/241

[56] References Cited

U.S. PATENT DOCUMENTS

| 344,984 | 7/1886 | Price | 128/5 |
|---|---|---|---|
| 348,843 | 9/1886 | Hamilton | 128/5 |
| 1,632,290 | 6/1927 | Heymer | 128/5 |
| 4,201,199 | 5/1980 | Smith | 128/7 |
| 4,620,547 | 11/1986 | Boebel | 128/4 X |

OTHER PUBLICATIONS

"Universal Subcutaneous Endoscope", Anthroscope, Journal of the Japanese Anthroscopic Association, vol. 12, No. 1, 1987, Ichiro Okutsu et al.
"Universal Endoscope", The Journal of the Japanese Orthopedic Association, vol. 61, No. 5, 1987, Ichiro Okutsu et al.

Primary Examiner—William H. Grieb
Attorney, Agent, or Firm—Skjerven, Morrill, MacPherson, Franklin & Friel

[57] ABSTRACT

An endoscope guide pipe includes a pipe member with a first end, which is closed and in a generally convergent, rounded shape, and a second end which is opposite to the first end and open. The pipe member is typically formed from a transparent material, such as a glass or plastic material. Thus, the guide pipe may be inserted into a body, and then an endoscope may be fitted into the guide pipe to observe the internal structure of the body. Since a defined space or cavity is maintained when the guide pipe is inserted into the body, so the internal structure of a body, such as a subcutaneous tissue, can be viewed directly by the endoscope in the present guide pipe. The guide pipe is particularly advantageous when it is desired to view directly a portion of a body which does not have a cavity or space, such as the internal structure of a muscle.

11 Claims, 7 Drawing Sheets

ENDOSCOPE GUIDE PIPE

BACKGROUND OF THE INVENTION

1. Field of the Invention

This invention generally relates to a medical instrument for observing the interior of a body, and, in particular, to a guide pipe particularly suitable for use with an endoscope for observing subcutaneous tissue. More specifically, the present invention relates to a medical guide pipe which may be used with an endoscope to observe tissue, such as a muscle, tendons and nerves, which is directly present under the skin and also to carry out a subcutaneous operation with a minimum of damage to the skin.

2. Description of the Prior Art

Figure 1:
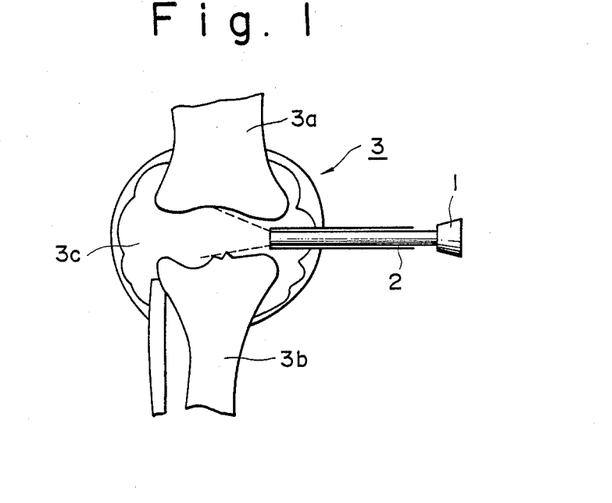
FIG. 1 is an illustration showing a typical usage of a prior art endoscope.

An endoscope is well known as a device for observing a space present in a body, such as a joint, abdominal cavity, bladder, stomach and intestines, and it is used widely in various medical fields, such as orthodpedic surgery, internal medicine, surgery, gynecology and urology. A typical method of using such an endoscope is illustrated in FIG. 1. As shown in FIG. 1, a space or cavity 3c is defined between a pair of oposing bones 3a and 3b at a joint 3 of a body, and an endoscope 1 is inserted into the space 3c of the joint 3 to observe the interior of the joint 3. The endoscope 1 is elongate in shape and fitted into a metal outer sleeve 2 for protection. An optical system is provided inside the endoscope 1 so that light is emitted forward from the tip end of the endoscope 1 for illuminating the space 3c. The illuminated space 3c is thus observed visually through an objective lens mounted at the tip end of the endoscope 1. However, in accordance with the prior art, the endoscope 1 was used only when it was desired to observe a portion of the body where there was a space or cavity, and it was impossible to directly observe subcutaneous tissue, such as a muscle, tendons, and nerves, using a prior art endoscope.

SUMMARY OF THE INVENTION

In accordance with the concept of the present invention, a guide pipe particularly suitable for use with an endoscope is provided consisting of an elongated pipe with one end closed and convergent in shape and the other end closed and with a transparent portion forming at least a part thereof. In one embodiment, the guide pipe is formed from a transparent glass material, such as pyrex, or a transparent plastic material. In this embodiment, if use is made of a so-called slant endoscope having a slant tip end, that portion of the subcutaneous tissue which is in direct contact with or located in the vicinity of the guide pipe can be viewed directly through an angle of 360° by rotating the slant endoscope as fitted in the guide pipe.

In another embodiment of the present invention, the present guide pipe is formed with at least one opening in the form of a slit or slot. With this structure, a surgical instrument, such as a surgical knife, may be fitted into the guide pipe and then projected radially outward from the guide pipe to carry out a subcutaneous operation with a minimum of damage to the skin. In the embodiment where the guide pipe is formed from a glass material, it is preferable to provide a plastic coating over at least a part of the glass guide pipe. Such a coating may be provided in any desired manner. With the provision of such a plastic outer coating, even if the glass guide pipe breaks for some reason, the fragments of the glass guide pipe are prevented from remaining inside the body.

Figure 2:
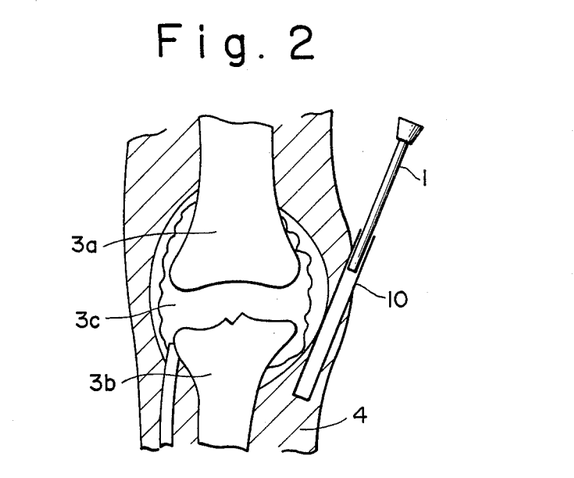
FIG. 2 is an illustration showing a typical example of how to use an endoscope guide pipe of the present invention.

FIG. 2 illustrates one example of how the guide pipe 10 of the present invention for use with an endoscope 1 may be used to visually observe the interior of a subcutaneous tissue 4 in the vicinity of a joint. The guide pipe 10 of the present invention shown in FIG. 2 is formed from a transparent glass or plastic material in its entirety. FIG. 2 shows the condition in which a part of the skin has been cut and the guide pipe 10 has been inserted into the subcutaneous tissue 4 near the joint. Under these conditions, if the endoscope 1 is fitted into the guide pipe 10, that portion of the subcutaneous tissue 4 which is in direct contact with or located in the vicinity of the guide pipe 10 can be observed directly. In this manner, even if a space or cavity does not exist within the body, the guide pipe 10 of the present invention can positively form a defined space or cavity, in particular within subcutaneous tissue. This invention thereby allows visual observation of the interior of a body through the present guide pipe, regardless of whether or not an interior space actually exists.

A primary object of the present invention is therefore to obviate the disadvantages of the prior art as described above and to provide an improved medical instrument for observing the interior of a body.

Another object of the present invention is to provide a medical guide pipe particularly suitable for use with an endoscope for visual observation of the internal structure of a body and, in particular of subcutaneous tissue.

A further object of the present invention is to provide an endoscope guide pipe which allows direct observation, with high resolution and accuracy, of virtually any portion of subcutaneous tissue.

Still another object of the present invention is to provide a surgical guide pipe which may be used together with an endoscope to directly observe the inside structure of a body and also to carry out a surgical operation on the inside structure of a body with a minimum of damage to the skin.

Other objects, advantages and novel features of the present invention will become apparent from the following detailed description of the invention, considered in conjunction with the accompanying drawings.

DESCRIPTION OF THE PREFERRED EMBODIMENTS

Figure 3A:
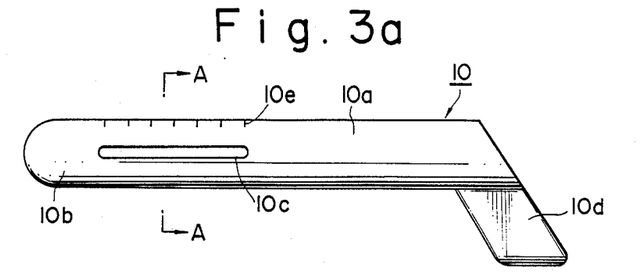
FIGS. 3a through 3c illustrate a guide pipe constructed in accordance with one embodiment of the present invention.
Figure 3B:
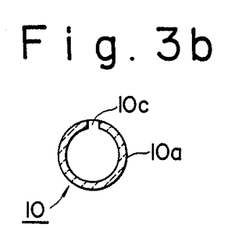
Figure 3C:
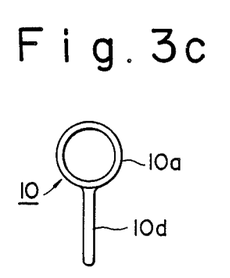

FIG. 3a, illustrates a guide pipe 10, particularly suitable for use as a guide pipe of an endoscope, constructed in accordance with one embodiment of the present invention. FIG. 3b is a cross-sectional view taken along the line A—A indicated in FIG. 3a, and FIG. 3c is a right-hand side elevational view of the guide pipe 10 shown in FIG. 3a. As shown, the guide pipe 10 of the present invention includes an elongated cylindrical member or pipe member 10a whose tip end 10b is closed, generally convergent in shape and rounded at the tip, and whose other end is open. In the illustrated embodiment, a slot 10c is formed in the pipe member 10a as extending in parallel with the longitudinal axis of the pipe member 10a, and, moreover, a scale 10e is also provided on the pipe member 10a. In addition, a handle 10d is integrally formed on the open end of the pipe member 10a as extending generally in the radial direction.

Preferably, the pipe member 10a is integrally formed from a transparent glass or plastic material. The pipe member 10a is generally cylindrical in shape and the inner diameter is set to be slightly larger than the outer diameter of an endoscope to be used therewith. Thus, after setting the present guide pipe 10 at a predetermined position as shown in FIG. 2, an associated endoscope may be inserted into the present guide pipe 10, so that the interior of a body, and in particular subcutaneous structure, can be observed.

Figure 4A:
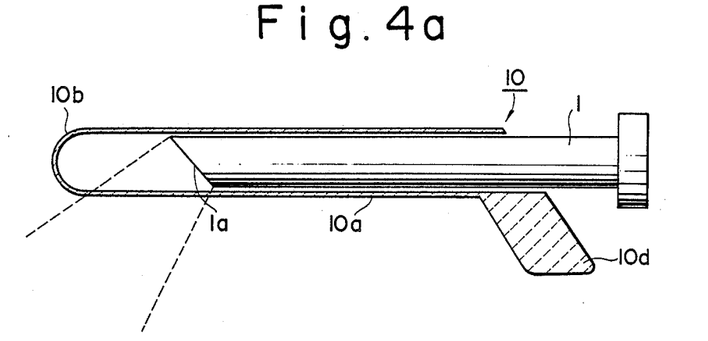
FIGS. 4a and 4b are illustrations showing examples of how to use the guide pipe shown in FIGS. 3a through 3c.
Figure 4B:
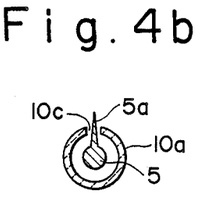

FIG. 4a illustrates the condition in which a so-called slant endoscope 1 having a slant tip end surface 1a is inserted into the present guide pipe 10. In this case, an object, such as a subcutaneous tissue, located in a region defined by the dotted lines indicated in FIG. 4a can be observed through the guide pipe 10. Further, since the slant endoscope 1 can be rotated around its longitudinal axis within the guide pipe 10 over 360°, an object located within a region of a cone defined by rotating the dotted lines shown in FIG. 4a around the longitudinal axis of the guide pipe 10 can be viewed. Thus, it is possible to observe the internal structure of a living body by the endoscope 1 fitted into the guide pipe 10 inserted in the body. In this case, if the scale 10e is provided on the pipe member 10a as shown in FIG. 3a, the location and size of an abnormal section of the internal structure of a body can be determined easily. If such an abnormal section has been found through observation using the endoscope 1, then the endoscope 1 is pulled out of the guide pipe 10, and a surgical instrument 5, such as a surgical knife, is fitted into the guide pipe 10. FIG. 4b illustrates the condition in which a surgical knife 5, has been inserted into the guide pipe 10 and a cutting edge 5a of the knife 5 has been projected out of the guide pipe 10 through the slot 10c in the radial direction. In this manner, and immediately after observation by the slant endoscope 1 and while keeping the guide pipe 10 in position, the endoscope 1 may be pulled out and the knife 5 may be fitted into the guide pipe 10 to carry out a desired operation on a desired portion, such as an abnormal section found during the observation, of the internal structure of a body.

As a specific example, for illustrative purposes only, the guide pipe 10 is integrally made of pyrex glass to have a thickness of approximately 1 mm and an internal diameter of approximately 5 mm. The guide pipe 10 may have a length of approximately 100 mm and the slot 10c may be approximately 30 mm in length and approximately 2 mm in width. It should be noted, however, that all of these specific dimensions are given, not for the purpose of limiting the scope of the present invention, but solely for illustrative purposes, and any other desired dimensions can be used.

Figure 5:
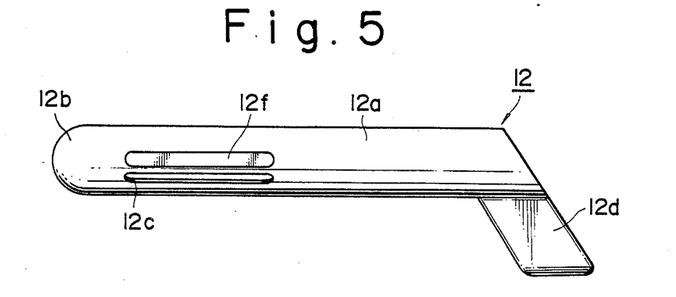
FIGS. 5 through 11 are schematic illustrations showing several other embodiments of the present invention.
Figure 6:
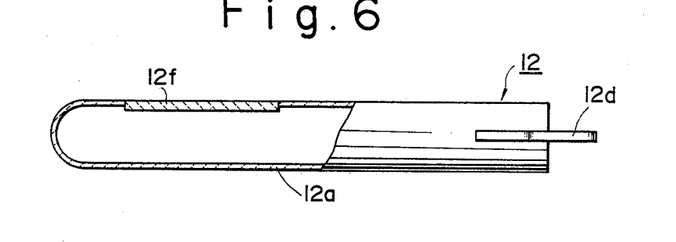

FIG. 5 illustrates a guide pipe 12 particularly suitable for use with an endoscope and constructed in accordance with another embodiment of the present invention. The guide pipe 12 includes a metal pipe member 12a which is generally cylindrical in shape and whose tip end 12b is closed, generally convergent in shape and rounded at the tip, and whose other end is open. The pipe member 12a is formed with a pair of slots side by side as extending along the longitudinal axis of the pipe member 12a. As shown in FIG. 6, one of the pair of slots is filled with a transparent material, such as a glass material, to define a window section 12f, and the other slot 12c defines an elongated opening. In addition, a holder 12d is integrally formed with the pipe member 12a. Since the window section 12f and the opening 12c become hidden when the present guide pipe 12 is set in position by insertion into a body, the angular position of both the window section 12f and the opening 12c may be determined by the angular position of the holder 12d. In the present embodiment, an observation of an object, such as a subcutaneous structure, can be made through the window section 12f, and, moreover, a directional observation can also be carried out through the opening 12c, if desired. In addition, a surgical instrument may be inserted into the pipe member 12a and projected out of the pipe member 12a via the opening 12c.

Figure 7:
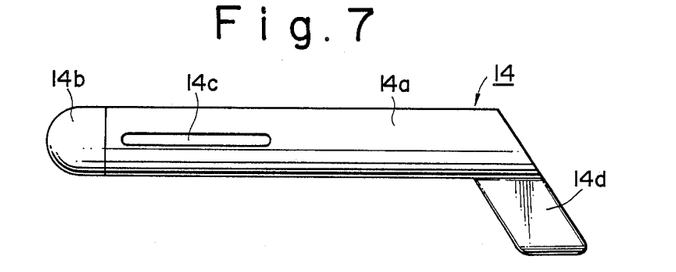

FIG. 7 illustrates a guide pipe 14 constructed in accordance with a further embodiment of the present invention. The guide pipe 14 of the present embodiment includes a metal cylindrical pipe member 14a and a convergent tip end member 14b which is comprised of a transparent material, such as glass or plastic, rounded at the tip and fixedly attached to the forward end of the pipe member 14a. Thus, the guide pipe 14 has basically a two-part structure. The pipe member 14a is formed with a slot 14c in the form of an elongated opening, and a holder 14d is integrally formed at the base end of the pipe member 14a. In the illustrated embodiment, the entire section of the rounded and generally convergent tip end member 14b is formed from a transparent material, so an internal structure of a body can be observed by an endoscope (not shown) fitted into the guide pipe 14. The pipe member 14a is formed with a slot 14c in the form of an elongated opening, so that an object can be viewed directly through the slot 14c, if desired. In addition, a surgical instrument can also be fitted into the pipe member 14a and projected out of the pipe member 14a through the slot 14c to carry out a desired surgical operation.

Figure 8:
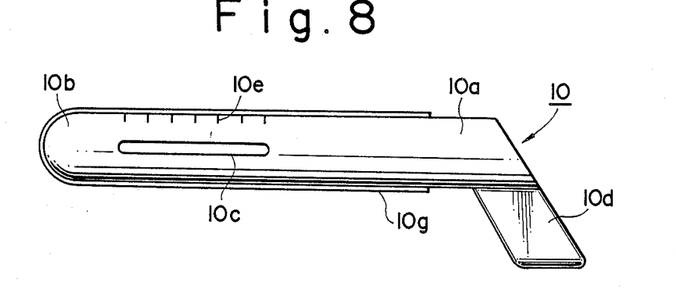

FIG. 8 illustrates a modification of the above-described embodiments. If the guide pipe 10 is partly or completely formed from a glass material, such as pyrex, there may be a case in which the guide pipe 10, or at least its glass portion, is broken. If the guide pipe 10 is broken while being inserted into a body, the clean-up process is rather complicated. Thus, in particular, if the guide pipe 10 is formed partly or wholly from glass material, a cover or coating 10g of a plastic or resin transparent material is provided to enclose at least that portion of the pipe member 10a and the tip end member 10b which is formed from a glass material. The cover 10g also covers the opening slot 10c; however, a surgical instrument, such as a surgicial knife, may be fitted into the pipe member 10a and pushed radially out of the slot 10c by partly breaking the cover 10g. Thus, this embodiment is particularly suitable for a disposable type guide pipe of the present invention.

Figure 9:
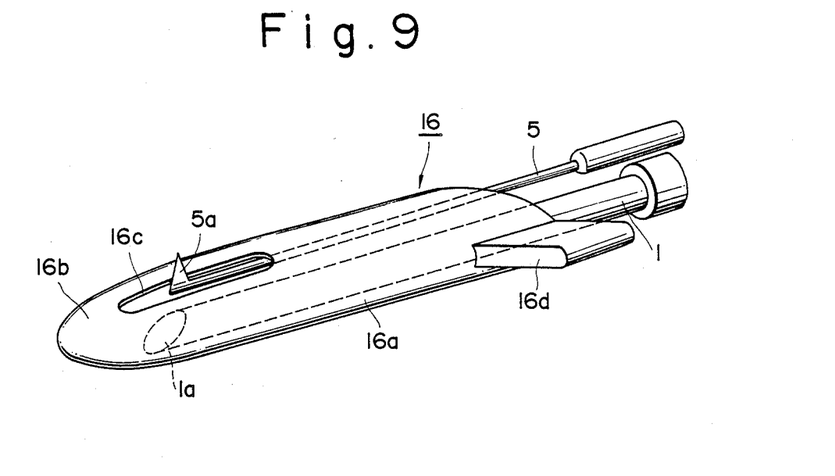
Figure 10:
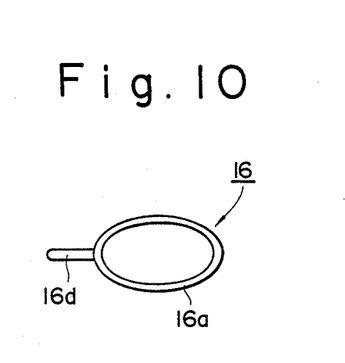
Figure 11:
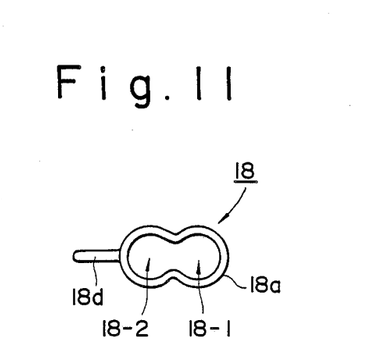

FIGS. 9 through 11 illustrate further modifications of the above-described embodiments of the present invention. In the above-described embodiments, an open slot is formed in the pipe member, so that a surgical instrument may be fitted into the pipe member and projected out of the pipe member through the open slot, in order to perform a surgical operation. In addition, the pipe member is partly or wholly formed from a transparent material, so that an object, such as a subcutaneous structure, can be observed by an endoscope fitted into the pipe member. Accordingly, if the inner diameter of a pipe member is set sufficiently large, an endoscope and a surgical instrument can both be fitted into the pipe member simultaneously, so observation and a surgical operation can be carried out at the same time.

In the embodiment of the present invention illustrated in FIGS. 9 and 10, there is schematically shown a guide pipe 16 constructed in accordance with still another embodiment of the present invention. As shown, the guide pipe 16 includes a pipe member 16a which is generally elliptic or oval in cross sectional shape, so that an endoscope 1 and a surgical instrument 5 can be fitted side by side into the pipe member 16a at the same time. Because of this particular cross-sectional shape of the pipe member 16, the dead space within the pipe member 16a is minimized. With this structure, the required cross-sectional area of the pipe member 16a is minimized, and this is particularly important because it will minimize the burden imposed upon a body when inserting the pipe member 16a into the body. The pipe member 16a is integrally formed with a rounded-tip convergent tip end member 16b at its forward end, and a holder 16d is also integrally formed at its base end. In addition, an open, elongated slot 16c is formed in the pipe member 16a, so that a cutting edge 5a of the surgical instrument 5 may be projected radially out of the pipe member 16a through this open slot 16c. The pipe member 16a is formed at least partly from a transparent material, such as glass or plastic.

FIG. 11 illustrates a guide pipe 18 constructed as a modification of the embodiment shown in FIGS. 9 and 10. In the embodiment of FIG. 11, the guide pipe 18 includes a pipe member 18a which has a cross-section generally in the shape of the numeral "8". In this case, the inner space of the pipe member 18a is generally divided into two compartments, i.e., a first compartment 18-1 for a surgical instrument 5 and a second compartment 18-2 for an endoscope 1. With this structure, the dead space inside of the pipe member 18a is minimized, and in addition, since the surgical instrument 5 and the endoscope 1 are fitted into the separate compartments of the pipe member 18a, interference between the surgical instrument 5 and the endoscope 1 can be avoided, thereby providing enhanced operability. It is to be noted that the pipe member 18a is also integrally formed with a rounded-tip, convergent tip end member at its forward end and with a holder 18d at its base end in a manner similar to that shown in FIG. 9.

Figure 12A:
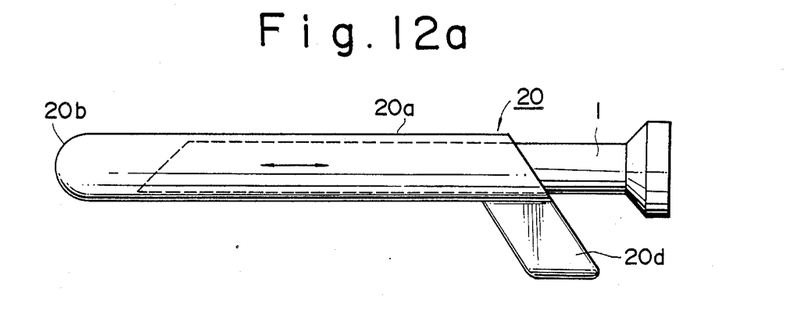
FIGS. 12a and 12b are schematic illustrations showing an endoscope guide pipe constructed in accordance with a further embodiment of the present invention.
Figure 12B:
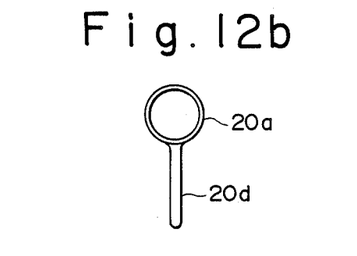

FIGS. 12a and 12b show a guide pipe 20 constructed in accordance with still a further embodiment of the present invention. The guide pipe 20 is similar in many respects to the embodiment shown in FIGS. 3a through 3c, except that no open slot is formed in the present guide pipe 20. As shown in FIGS. 12a and 12b, the guide pipe 20 includes a pipe member 20a having a forward end which is closed by a generally convergent rounded tip portion 20b and a base end which is open. The pipe member 20a is formed with a handle 20d. The pipe member is entirely formed from a transparent material, such as glass or plastic. The pipe member 20a has an inner diameter set large enough for an endoscope 1 to be rotatable and slidable when fitted therein. Thus, as indicated by the double-sided arrow in FIG. 12a, the endoscope 1 inside the guide pipe 20 may slide along the longitudinal axis of the pipe member 20a. If desired, a scale may be provided on the pipe member 20a. The guide pipe 20 of the present embodiment is used exclusively for the purpose of observing an internal structure of a body by means of an associated endoscope 1 as fitted in the guide pipe 20.

Figure 13:
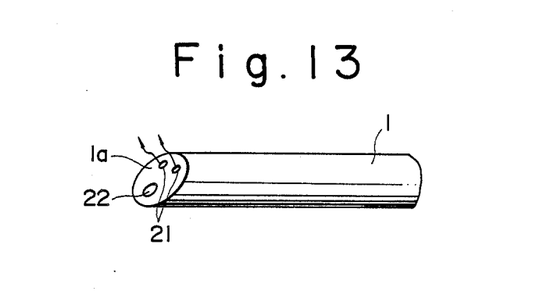
FIGS. 13 and 14 are schematic illustrations showing a few examples of the structure of an endoscope 1 which may be advantageously used with the present guide pipe.
Figure 14:
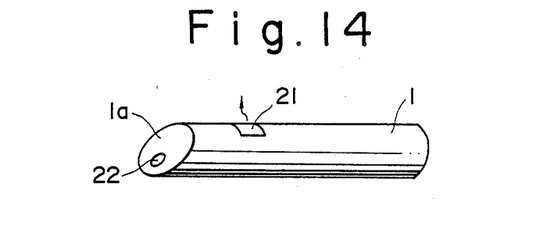

FIG. 13 schematically illustrates the tip end portion of an endoscoope 1 which may be advantageously used with a guide pipe of the present invention. As shown, the illustrated endoscope 1 has a slanted forward end surface 1a, so that the endoscope 1 may be called a "slant endoscope". A pair of light-emitting portions 21 and 21 are formed at the slant forward end surface 1a. Also formed at the surface 1a is a light-receiving portion 22 for receiving the light emitted from the light-emitting portions 21 and 21 after having been reflected by an object, such as an internal structure of a body. Typically, an objective lens is disposed at the light-receiving portion 22 of the slant surface 1a. Such an endoscope 1 may slide along and rotate around the longitudinal axis of the pipe member 20a, allowing an object, such as an internal structure of a body located adjacent to the pipe member 20a, to be viewed directly. FIG. 14 illustrates a modified version of an endoscoope 1 in which a light-receiving portion 22 is provided at the slanted forward end surface 1a, and a light-emitting portion 21 is provided at the peripheral outer surface of the endoscope 1. With this structure, the light emitted from the light-emitting portion 21 on the outer peripheral surface of the endoscope 1 is introduced into and transmitted along the pipe member 20a, which is formed from a transparent material, such as glass. The pipe member 20a is thereby used as a light-transmitting guide, so that the light emitted from the light-emitted portion 21 is transmitted to the pipe member 20a uniformly to illuminate an object, such as an internal structure of a body, located adjacent to the pipe member 20a. Thus, this structure allows use of the entire area of the slant forward surface 1a as the light-receiving portion 22, if desired.

Figure 15:
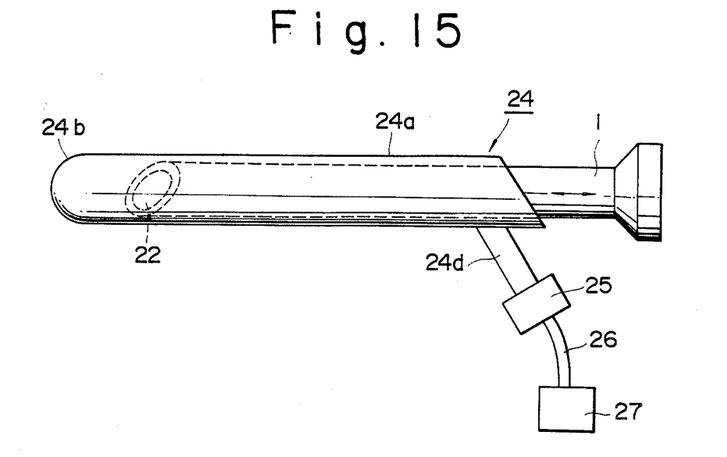
FIG. 15 is a schematic illustration showing a guide pipe which may be constructed as a modification of the guide pipe shown in FIG. 12.

FIG. 15 schematically illustrates a further modified version of the embodiment shown in FIGS. 12a and 12b. A guide pipe 24 illustrated in FIG. 15 generally has a structure similar to the guide pipe 20 illustrated in FIG. 12a; however, the guide pipe 24 shown in FIG. 15 has its handle 24d coupled to an optical coupler 25, which, in turn, is operatively coupled to a light source 27 via fiber optics 26. Thus, the guide pipe 24 of the present embodiment has a light-transmitting function, and so when inserted into the interior of a body, it illuminates an object adjacent thereto. As a result, with this structure an endoscope 1 fitted into this guide pipe 24 is not required to be provided with a light source and/or a light-transmitting medium incorporated therein, but must only be provided with a light-receiving portion 22 and an associated optical system. Thus, the endoscope 1 to be used with this guide pipe 24 may be made extremely smaller in size, which, in turn, allows the present guide pipe 24 also to be made much smaller. It should be noted that the guide pipe 24 also includes a pipe member 24a which is generally cylindrical in shape, with a round, convergent forward end 24b and an open base end.

Figure 16:
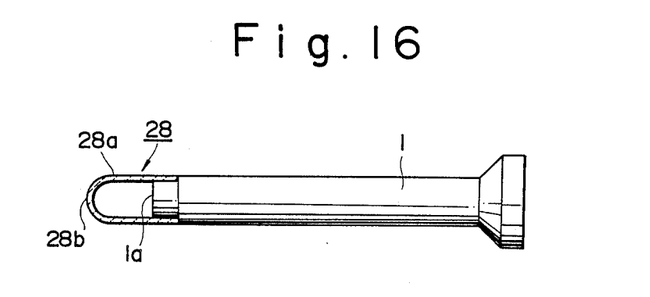
FIGS. 16 and 17 are schematic illustrations showing an embodiment in which the present guide pipe is fixedly attached to an endoscope.
Figure 17:
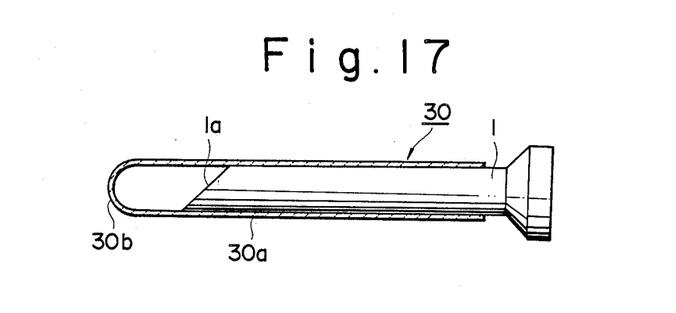

FIGS. 16 and 17 schematically illustrate fixed guide pipes 28 and 30, respectively, in which each of the guide pipes 28 and 30 is attached to its associated endoscope 1 at its forward end. The guide pipe 28 shown to FIG. 16 is fitted on and attached to, for example, by means of an adhesive or any other means for attachment, the forward end of an endoscope 1. In another embodiment, the guide pipe 30 of FIG. 17 is fitted onto and attached to a substantial portion of the endoscope 1. The guide pipe 28 includes a pipe member 28a of a generally cylindrical shape and the forward end of the pipe member 28a is closed, rounded, and generally convergent in shape. Similarly, the guide pipe 30 of FIG. 17 also includes a pipe member 30a which is generally cylindrical and which has a tip end portion 30b which is rounded and generally convergent in shape. It is important to note that, there is a fixed space in front of the forward end surface 1a of the endoscope 1 provided by the guide pipe 28 or 30, so that an object located adjacent to or in contact with the guide pipe 30 can be viewed with high precision and resolution. Otherwise, an object will come in contact with the end surface 1a of the endoscope 1, in which case the object cannot be viewed by the endoscope 1. In the preferred embodiment, the fixed space is filled with liquid, such as a saline solution.

Figure 18:
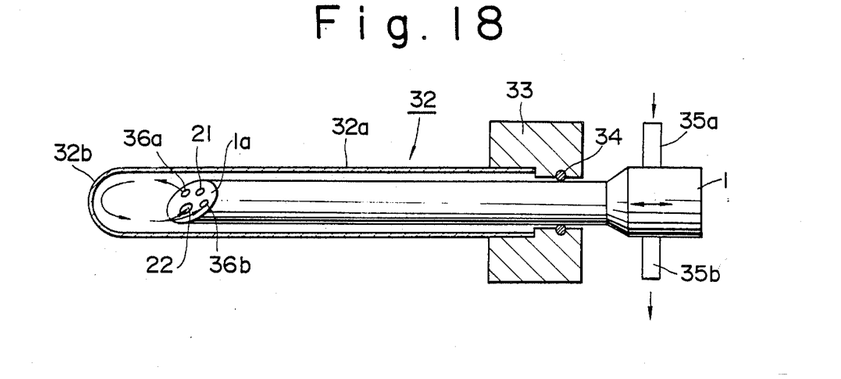
FIGS. 18 and 19 are schematic illustrations showing other embodiments of the present invention in which a flow of liquid is formed inside a guide pipe.
Figure 19:
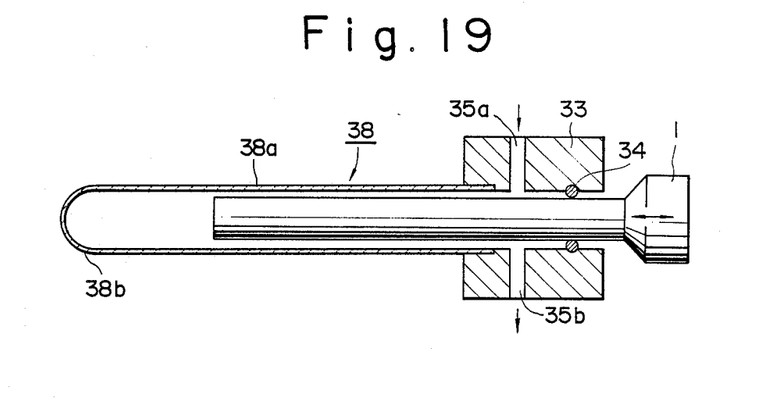
Figure 20:
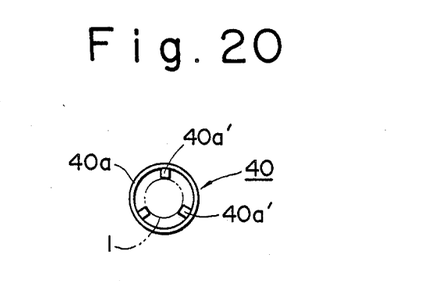
FIG. 20 is a schematic illustration showing a still further embodiment of the present invention.

FIGS. 18 through 20 illustrate still further embodiments of the present guide pipe. That is, in the embodiment shown in FIG. 18, a guide pipe 32 includes a pipe member 32a which is generally cylindrical in shape and formed from a transparent material, and which has a rounded and generally convergently shaped forward end 32b and an open opposite end to allow an endoscope 1 to be fitted into the guide pipe 32. The guide 32 is supported by a support block 33, and the endoscope 1 is fitted and sealed into the guide pipe 32 by means of an O-ring 34 mounted on the support block 33. The endoscope 1 is provided with an inlet 35a and an outlet 35b at its base end for liquid, such as a saline solution. Thus, the liquid supplied from an external supply source into the endoscope 1 through the inlet 35a is introduced into the guide pipe 32 through a supply line in the endoscope 1 and enters through a discharge port 36a formed at the forward end surface 1a. The liquid thus discharged into the guide pipe 32 flows as indicated by the arrows. Then, the liquid flows into a discharge line provided in the endoscope 1 through a suction port 36b and then discharged to the exterior via the outlet 35b. In this manner, the liquid, such as a saline solution, flows within the guide pipe 32, so that the inner surface of the guide pipe 32 is kept clean at all times. This is advantageous because water droplets may form on the inner surface of the guide pipe 32, which scatter light and obstruct the view of an object in contact with or adjacent to the guide pipe 32.

FIG. 19 shows a modified version of the embodiment shown in FIG. 18. A guide pipe 38 of the present embodiment includes a pipe member 38a which is formed from a transparent material and generally cylindrical in shape. The pipe member 38a has a closed forward end 38b with a round tipped, generally convergent shape. The pipe member 38a has an opposite base end which is attached to the support block 33. One difference from the previous embodiment shown in FIG. 18 is that the inlet 35a and outlet 35b are formed in the support block 33. Thus, liquid is introduced into the interior of the guide pipe 38 from an external supply source through the inlet 35a, and the liquid inside of the guide pipe 38 is discharged to the exterior through the outlet 35b. In this case, there is no need to provide liquid supply and discharge lines inside of the endoscope 1, which allows the endoscope 1 and the guide pipe 38 to be smaller. In addition, in order for the liquid flowing into the guide pipe 38 through the inlet 35a to flow toward the tip end 38b of the guide pipe 38 effectively, it is preferable to provide means for controlling the flow direction of the liquid in at least one of the following structures: the support block 33, the inner surface of the guide pipe 38, or the outer surface of the endoscope 1.

FIG. 20 schematically illustrates a guide pipe 40 constructed in accordance with a further embodiment of the present invention. The guide pipe 40 of the present embodiment also includes a pipe member 40a, which is comprised of a transparent material at least in part and is generally cylindrical in shape, with a round tipped generally convergently shaped forward end and an open opposite end to allow an endoscope to be fitted into the guide pipe 40. In the present embodiment, a plurality of projections 40a', which project radially inward from at least three angular locations on the inner peripheral surface of the pipe member 40a. The endoscope 1 fitted into the guide pipe 40 is supported at a predetermined position inside of the guide pipe 40 through sliding contact with the tip ends of these projections 40a'. Such a structure is particularly advantageous because the endoscope 1 is kept in a predetermined relative position with respect to the guide pipe 40, and the sliding movement of the endoscope 1 with respect to the guide pipe 40 will occur more smoothly. It should be noted that the structure shown in FIG. 20 may be applied to any of the previously described embodiments of the present invention as an additional feature.

While the above provides a full and complete disclosure of the preferred embodiments of the present invention, various modifications, alternate constructions and equivalents may be employed without departing from the true spirit and scope of the invention. For example, an anti-reflection coating may be provided on at least one of the inner and outer surfaces of a transparent section of a guide pipe of the present invention. Therefore, the above description and illustration should not be construed as limiting the scope of the invention, which is defined by the appended claims.

What is claimed is:

1. A medical instrument for guiding an endoscope to be inserted therein for viewing a subcutaneous structure of a body, comprising:
   an endoscope; and an elongated pipe member having a first end, which is closed and generally convergent in shape, and a second end, which is opposite said first end and which is open, thereby allowing said endoscope to be loosely fitted into said pipe member to permit said endoscope to rotate around a longitudinal axis thereof as being located inside of said guide pipe, said elongated pipe member including a transparent portion comprising at least a predetermined part thereof.

2. The medical instrument of claim 1, wherein said convergent first end is generally rounded, thereby substantially eliminating any sharp corner.

3. The medical instrument of claim 1, further comprising a handle integrally formed with said pipe member and extending radially outwardly from said pipe member.

4. The medical instrument of claim 1, wherein said pipe member is formed from a transparent glass material.

5. The medical instrument of claim 1, wherein said pipe member is formed from a transparent plastic material.

6. The medical instrument of claim 1, wherein said pipe member is formed with at least one opening.

7. The medical instrument of claim 1, wherein said pipe member is provided with at least one scale.

8. The medical instrument of claim 1, wherein said pipe member is so structured that the endoscope fitted into said pipe member may be moved slidably freely along the longitudinal axis of said pipe member.

9. The medical instrument of claim 1, wherein said pipe member is formed from a metal at least in part, and said pipe member is formed with at least one opening.

10. The medical instrument of claim 1, wherein a gap between said guide pipe and said endoscope loosely fitted in said guide pipe is filled with liquid.

11. The medical instrument of claim 10, further comprising:
    support means for fitting said endoscope into said guide pipe,
    external liquid supply means for providing said liquid to said gap through said support means, and
    external liquid discharge means for removing said liquid from said gap through said support means.

* * * * *